United States Patent
Dasai et al.

(10) Patent No.: US 9,766,202 B2
(45) Date of Patent: Sep. 19, 2017

(54) METHOD FOR DETECTING CHEMICAL AND PHYSICAL PHENOMENON, AND DEVICE THEREFOR

(75) Inventors: Fumihiro Dasai, Toyohashi (JP); Kazuaki Sawada, Toyohashi (JP)

(73) Assignee: National University Corporation Toyohashi University of Technology (JP)

(*) Notice: Subject to any disclaimer, the term of this patent is extended or adjusted under 35 U.S.C. 154(b) by 696 days.

(21) Appl. No.: 14/131,391

(22) PCT Filed: Jul. 13, 2012

(86) PCT No.: PCT/JP2012/067908
§ 371 (c)(1),
(2), (4) Date: Jan. 7, 2014

(87) PCT Pub. No.: WO2013/008908
PCT Pub. Date: Jan. 17, 2013

(65) Prior Publication Data
US 2014/0139231 A1 May 22, 2014

(30) Foreign Application Priority Data
Jul. 14, 2011 (JP) ................. 2011-155688

(51) Int. Cl.
*G01N 27/416* (2006.01)
*G01N 27/414* (2006.01)
*H01L 27/146* (2006.01)

(52) U.S. Cl.
CPC ..... *G01N 27/4167* (2013.01); *G01N 27/4148* (2013.01); *H01L 27/14609* (2013.01); *H01L 27/14641* (2013.01)

(58) Field of Classification Search
CPC ............ G01N 27/4167; G01N 27/4148; H01L 27/14641; H01L 27/14609
See application file for complete search history.

(56) References Cited

U.S. PATENT DOCUMENTS 6,294,133 B1    9/2001   Sawada et al.
7,424,372 B2 *   9/2008   Mimura ............. G01N 27/4148
                                                            257/253

(Continued)

FOREIGN PATENT DOCUMENTS

EP       1870703      12/2007
JP    2002221510 A    8/2002

(Continued)

OTHER PUBLICATIONS

Nishiguchi Katsuhiko et al., "Si nanowire ion-sensitive field-effect transistors with a shared floating gate", Applied Physics Letters, American Institute of Physics, US, vol. 94, No. 16, Apr. 21, 2009.

(Continued)

*Primary Examiner* — Robert Carpenter
(74) *Attorney, Agent, or Firm* — Quarles & Brady LLP; Gavin J. Milczarek-Desai

(57) ABSTRACT

Provided are a device for detecting chemical and physical phenomenon suitable for high integration, and a method therefor. Rather than using a TG section signal to select pixels that require charge measurement, the on-off timing (the timing for moving the charge from a sensing section to an FD section) of the TG section is harmonized for all pixels, and the release or injection of the charge to the sensing section is separately controlled, whereby the charge is held only in sensing sections of pixels that require charge measurement, and the charge is emptied in sensing sections of pixels that do not require charge measurement. In this state, the TG section of all pixels can be opened at the same time, whereby the charge is transferred to the FD section from only the sensing sections holding a charge, and the charge level of the pixel is detected.

7 Claims, 18 Drawing Sheets

(56) References Cited

U.S. PATENT DOCUMENTS

| | | | |
|---|---|---|---|
| 7,465,915 B2 | 12/2008 | Sawada et al. | |
| 7,728,898 B2 * | 6/2010 | Lee | H01L 27/14609 257/239 |
| 7,826,980 B2 | 11/2010 | Sawada et al. | |
| 8,023,468 B2 | 9/2011 | Liu et al. | |
| 2006/0266922 A1 | 11/2006 | McGrath et al. | |
| 2007/0215970 A1 | 9/2007 | Lee et al. | |
| 2008/0225148 A1 | 9/2008 | Parks | |
| 2010/0230579 A1 | 9/2010 | Watanabe | |
| 2010/0245648 A1 | 9/2010 | Tayanaka | |
| 2011/0174987 A1 | 7/2011 | Sawada et al. | |
| 2011/0236263 A1 | 9/2011 | Sawada et al. | |
| 2012/0002201 A1 | 1/2012 | Sawada et al. | |

FOREIGN PATENT DOCUMENTS

| | | |
|---|---|---|
| JP | 2004028723 A | 1/2004 |
| JP | 3623728 B2 | 2/2005 |
| JP | 4073831 B2 | 4/2008 |
| JP | 200879306 A | 4/2008 |
| JP | 4133028 B2 | 8/2008 |
| JP | 4171820 B2 | 10/2008 |
| JP | 4183789 B2 | 11/2008 |
| JP | 2009236502 A | 10/2009 |
| WO | 2007108465 A1 | 9/2007 |
| WO | 2009081890 A1 | 7/2009 |
| WO | 2009151004 A1 | 12/2009 |
| WO | 2010106800 A1 | 9/2010 |

OTHER PUBLICATIONS

Supplementary European Search Report dated Feb. 2, 2015; EP Application No. 12811391.7.
International Search Report for PCT/JP2012/067908 with English Translation.
Written Opinion for PCT/JP2012/067908 with English Translation.
Hiwaza et al., Fabrication of a two-dimensional pH image sensor using a charge transfer technique, Sensors and Actuators B: Chemical, Oct. 12, 2006 vol. 117 Issue 2 pp. 509-515.
Lee et al., Fabrication of a highly sensitive penicillin sensor based on charge transfer techniques, Biosensors and Bioelectronics, Mar. 15, 2009 vol. 24 Issue7 pp. 1877-1882.

* cited by examiner

METHOD FOR DETECTING CHEMICAL AND PHYSICAL PHENOMENON, AND DEVICE THEREFOR

FIELD OF THE INVENTION

The present invention relates to improvements in a chemical and physical phenomenon detecting device and a method for detecting a chemical and physical phenomenon.

BACKGROUND OF THE INVENTION

As to a chemical and physical phenomenon detecting device which is sometimes referred to as "a detecting device" hereinafter, the detecting device utilizing a floating diffusion which is sometimes referred to as "a FD section" hereinafter has been proposed as referred to patent documents 1-8.

For example, as shown in FIG. 1, such a detecting device is provided with a sensing section 10, a charge supply section 20, a charge transfer storage section 30, a charge quantity detecting section 40 and a charge eliminating section 50.

The sensing section 10 is provided with a sensing film 12 for changing a potential correspondingly to a detected object and a reference electrode 13. In accordance with the potential change of the sensing film 12, the depth of the potential well 15 is changed in a region, namely a p-type diffusion region 72 of a silicon substrate 71 faced with the sensing film 12.

The charge supply section 20 is provided with an injection diode section 21 sometimes referred to as "ID section" hereinafter and an input control gate section 23 sometimes referred to as "ICG section" hereinafter. The ID section 21 is charged with a charge. Then, with the potential of the ICG section 23 controlled, the charge in the ID section 21 is transferred to the potential well 15 of the sensing section 10.

The charge transfer storage section 30 is provided with a transfer gate section 31 sometimes referred to as "TG section" hereinafter and a floating diffusion section 33 sometimes referred to as "FD section". With the voltage of the TG section 31 controlled to change a potential of a region of the silicon substrate 71 which is faced with the TG section 31, the charge charged in the potential well 15 of the sensing section 10 is transferred to the FD section 33 and stored in the FD section 33.

The charge stored in the FD section 33 is detected by a charge quantity detecting section 40. As such a charge quantity detecting section 40, a source follower type signal amplifier can be used.

The charge eliminating section 50 is provided with a reset gate section 51 sometimes referred to as "RG section" and a reset drain section 53 sometimes referred to as "RD section". With the voltage of the RG section 51 controlled to change a potential of a region of the silicon substrate 71 which is faced with the RG section 51, the charge stored in the FD section 33 is transferred to the RD section 53 and discharged from the RD section 53.

The detailed structure and the behavior of such the detecting device are explained in the following by referring to a pH sensor for detecting the concentration of hydrogen ions as an example. As explained in the following, an electron is used as a charge. The subject region of the substrate 71 is doped suitably for transferring the electron.

The detecting device used for the pH sensor has an n-type silicon substrate 71. A predetermined region of the silicon substrate 71 is doped to form a p-well which constitutes a p-type diffusion region 72 corresponding to the sensing section 10. As to the p-well region, with n-type dopant diffused, n+ regions 74 and 75 are formed so as to put the p-type diffusion region 72 between the n+ regions 74 and 75. In addition, an n+ region 77 is formed at a predetermined distance from the n+ region 75. The n+ regions 74, 75 and 77 correspond to the ID section 21, the FD section 33 and the RD section 53 respectively.

The surface of the p-type diffusion region 72 is doped by n-type dopant to form an n-type region 73.

On the surface of the silicon substrate 71, a protective film 81 made of oxide silicon is formed. On the protective film 81, the electrode of the ICG section 23, the electrode of the TG section 31 and the electrode of the RG section 51 are put. When each of the electrodes are applied with voltage, the potential of each region of the silicon substrate 71 faced with each of the electrodes is changed.

In the sensing section 10, the sensing film 12 made of silicon nitride is put on the protective film 81.

As referred to FIG. 2, the basic behavior of the detecting device 1 is explained in the following.

When a solution which is a detected object contacts the sensing section 10, the depth of the potential well 15 of the sensing section 10 changes in accordance with the concentration of hydrogen ions, as referred to the step (A). Namely, the larger the concentration of hydrogen ions becomes, the deeper the potential well 15 becomes. In other words, the bottom of the potential becomes high.

On the other hand, the ID section 21 is charged with a charge by decreasing the potential of the ID section 21, as referred to the step (B). At the same time, the charge charged in the ID section 21 overflows the ICG section 23 to fill the potential well 15 of the sensing section 10. By the way, the potential of the TG section 31 is lower than the potential of the ICG section 23. So, the charge charged in the potential well 15 does not overleap the TG section 31 to reach the FD section 33.

Next, with the potential of the ID section 21 increased, the charge is extracted from the ID section 21. The charge slashed off by the ICG section 23 is left in the potential well 15, as referred to the step (C). Here, the charge quantity left in the potential well 15 corresponds to the depth of the potential well 15, namely the concentration of hydrogen ions which is the detected object.

Next, with the potential of the TG section 31 increased, the charge left in the potential well 15 is transferred to the FD section 33, as referred to the step (D). Thus, the charge stored in the FD section 33 is detected by the charge quantity detecting section 40, as referred to the step (E). Then, with the potential of the RG section 51 increased, the charge of the FD section 33 is evacuated to the RD section 53, as referred to the step (F). The RD section 53 is connected to VDD which absorbs the negative charge.

RELATED ART DOCUMENT

Patent Document

Patent document 1: JP-B-4171820
Patent document 2: JP-A-2008-79306
Patent document 3: JP-B-4073831
Patent document 4: JP-B-4183789
Patent document 5: JP-B-4133028
Patent document 6: WO/2009/081890A1
Patent document 7: WO/2010/106800A1
Patent document 8: WO/2009/151004A1

DISCLOSURE OF THE INVENTION

Problems to be Solved by the Invention

The pH detecting device described above has a constitution that various electrodes and a sensing film are formed on a silicon substrate. So, the pH detecting device can be integrated into a two-dimensional device which can detect two-dimensional pH distribution to output the two-dimensional pH distribution as an image.

In depicting such an image, since each of the pH detecting devices corresponds to one pixel, highly-integrated pH detecting devices are required.

The circuit configuration of the pH detecting device shown in FIG. 1 is shown in FIG. 3. As shown in FIG. 3, in each pixel, one sensing section, five transistors and seven wirings are required.

Thus, a number of elements required for one pixel prevent high-integration.

Means for Solving the Problems

The inventors of the present invention have studied to solve the problems. At the beginning, the inventors studied the common use of the transistors related to a source follower circuit 41 and a reset circuit 53. Then, the inventors found if the transistors which constitute the source follower circuit 41 and the reset circuit 53 are shared in common, the number of the transistors per pixel can be reduced effectively as shown in FIG. 4.

Namely, the charge transferred from each pixel of each sensing circuit to each FD section is sent to the common source follower circuit 141 to output the value to the output line OUT correspondingly to the charge quantity. By the way, the output timing is synchronized with the readout signal inputted for the readout line WL. The charge stored in the FD section is evacuated to the VDD (RD) through the reset circuit 153. The on and off of the reset circuit 153 are controlled by the signal of the RG control line.

For example, in conventional technique, five installed transistors are required per pixel. However, when the source follower circuit and so forth are commonly used in two pixels, the number of transistor becomes 3.5 per pixel if the number of the totally installed transistors is divided by the two pixels. Ina similar way, when the source follower circuit and so forth are commonly used in four pixels, the number of transistor becomes 2.75 per pixel if the number of the totally installed transistors is divided by the four pixels.

Accordingly, the number of the installed transistors is reduced to realize the constitution suited for the high-integration.

However, if the pixels which use the transistors commonly cooperate together, the pixel density deteriorates. So, it is sometimes desired that the charge quantity is detected by a pixel unit.

Then, the TG section is desired to control so that the charge is transferred to the FD section only from the sensing section provided with the selected pixel.

Thus, each TG section signal is allotted to each pixel. Therefore, each TG section control line is connected independently to the TG section of each pixel, as referred to FIG. 4.

The independent TG section control line connected to the TG section of each pixel leads to the increase of the wiring area, which could prevent the high-integration.

So, the inventors discard the TG section signal for selecting the pixel necessary for detecting the charge. The opening and the closing timings of the TG section for transferring the charge from the sensing section to the FD section are executed simultaneously in all of the pixels. Then, the charge injection into the sensing section and the charge evacuation are controlled separately from the TG section so that the charge is held only in the sensing section provided with a pixel necessary for detecting the charge. On the other hand, the pixel which is not necessary for detecting the charge is placed in a state with no charge.

In these circumstances, when the TG section is opened simultaneously in all of the pixels, the charge is transferred to the FD section only from the sensing section holding the charge, so that the charge quantity of the pixel can be detected.

Thus, the simultaneous opening and closing timings of the TG section make the independent TG section control lines unnecessary, to suppress the increase of the wiring region. Further, the charge injection into the sensing section and the charge evacuation can be executed by the control of the charge supply section 20. So, the number of the transistors and the wirings does not increase.

The first aspect of the present invention is conceived from the study described above and defined as the following, namely a method for controlling a chemical and physical phenomenon detecting device provided with a plurality of sensing sections for changing each bottom potential of each potential well correspondingly to a chemical and physical phenomenon which is a detected object, the chemical and physical phenomenon detecting device transferring a charge of each of the sensing sections to an FD section corresponding to each of the sensing sections through a TG section for identifying the chemical and physical phenomenon on a basis of a charge stored in the FD section, comprising the steps of:

holding a charge in a first potential well of a first sensing section selected from the sensing sections, and holding no charge in a second potential well of a second sensing section not selected from the sensing sections; and setting a condition for allowing a transfer of the charge from the first potential well and the second potential well simultaneously to one FD section of the FD section.

According to the first aspect of the present invention defined above, when each of the TG sections is opened and closed at the same timing, the charge is held in the first potential well of the first sensing section of the pixel selected, and the charge is made empty in the second potential well of the second sensing section of the pixel not selected. So, even if all of the TG sections are opened simultaneously, the charge is transferred to the FD section only from the first sensing section of the pixel selected, to detect the charge quantity stored in the first sensing section.

Thus, the TG section control line independently controlled per pixel becomes unnecessary to suppress the increase of the wiring region, as referred to FIG. 5. Incidentally, in FIG. 5, the same element as that of FIG. 4 is referred to the same reference numeral as that of FIG. 4 and the description thereof is eliminated.

In other words, if the first TG section for controlling the transfer of the charge from the one sensing section of the two sensing sections and the second TG section for controlling the transfer of the charge from the other sensing section of the two sensing sections are opened at the same timing, the charge is transferred from each of the sensing section to the FD section. So, it is not necessary to provide the two sensing sections.

Accordingly, at first, the one sensing section is made active and the other sensing section is made non-active. Next, the one sensing section is made non-active and the other sensing section is made active. Then, even if the first TG section and the second TG section are opened simultaneously, the charge quantity of each sensing section can be detected.

In the present invention, on condition that the TG section is opened and closed at the same timing, the sensing section is selectively made active or non-active. Incidentally, the active sensing section is defined as the first sensing section, and the non-active sensing section is defined as the second sensing section. Even if the sensing sections have the physically same structure, each of the sensing sections is defined as the first sensing section or the second sensing section dependently on the state of the sensing sections.

In the conventional detecting device, the sensing section is always made active. So, in the present invention, the sensing section may be made active by using the conventional technique.

On the other hand, the method that the sensing section is made non-active is newly proposed for the first time in the present specification.

One method includes the steps of supplying the charge once to all of sensing sections and making the potential of the ICG section high to evacuate the charge from the desired sensing section not selected, thereby making the sensing section non-active.

Another method includes the step of making the potential of the ICG section low correspondingly to the desired section not selected, to prohibit the charge supply from the ID section to the sensing section in itself.

EMBODIMENTS

A way for filling only the first sensing section with a charge and emptying a charge out of the second sensing section is explained in the following.

Namely, in an embodiment of the present invention, the charge is supplied for both of the first sensing section and the second sensing section. Then, the charge is eliminated only from the second sensing section.

Figure 1:
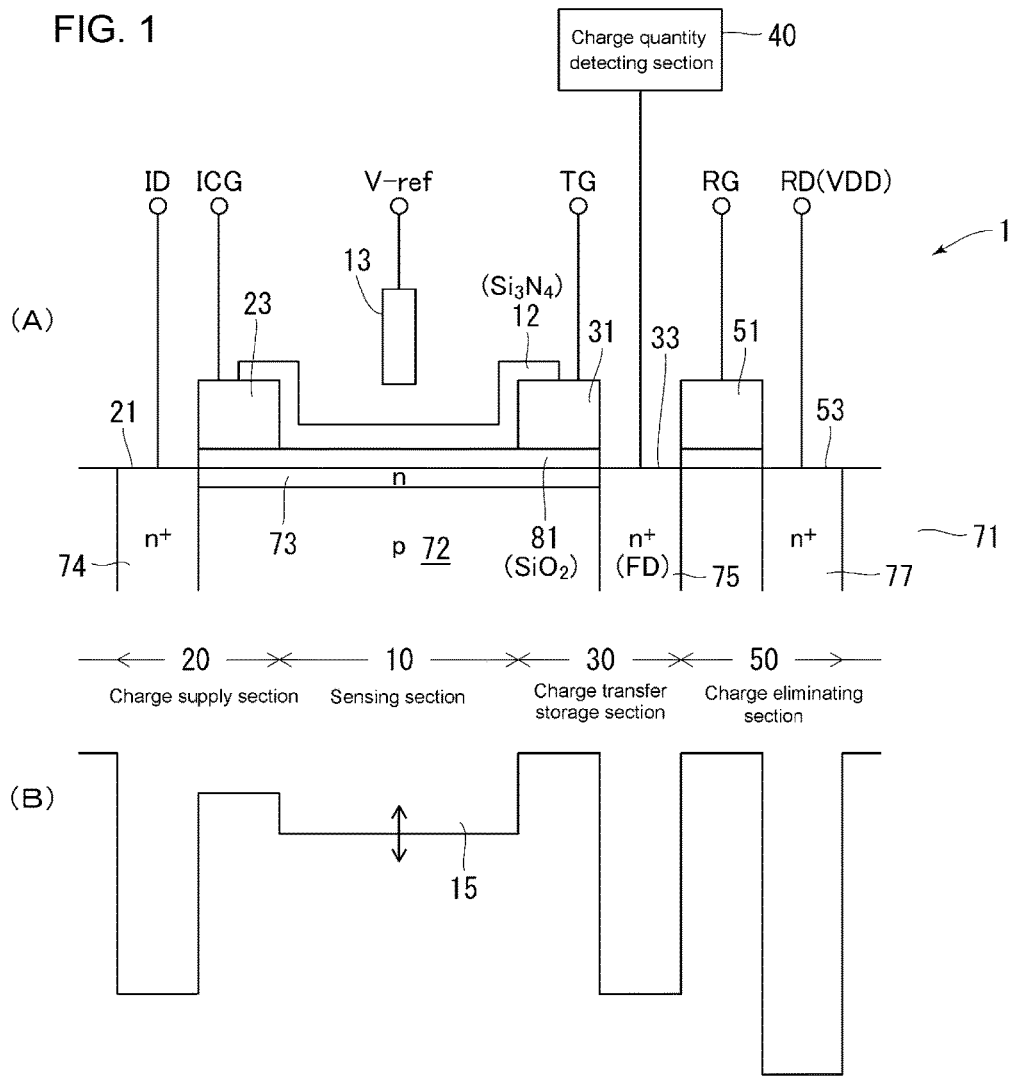
FIG. 1 shows a schematic configuration of a conventional detecting device.
Figure 2:
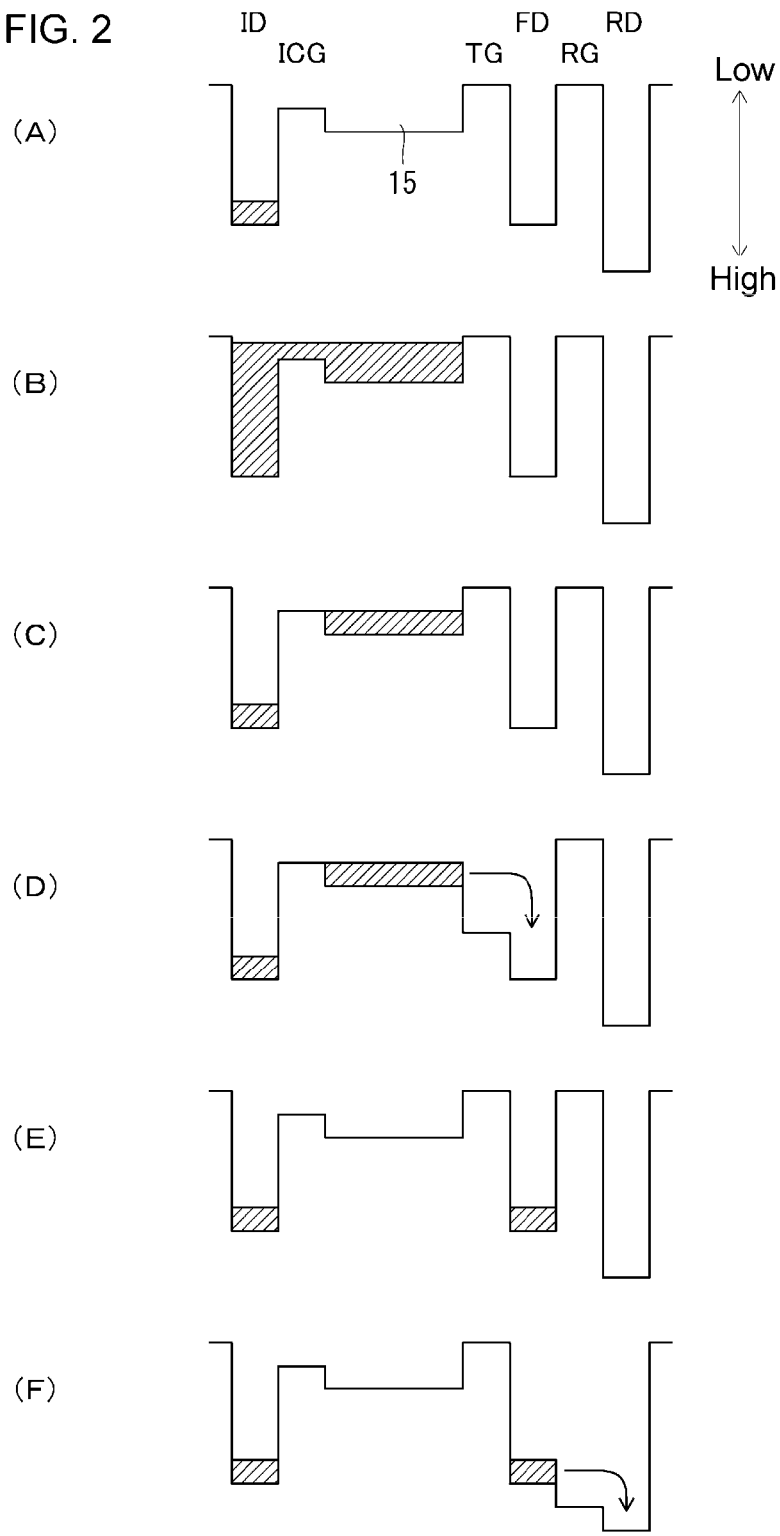
FIG. 2 is an operation flow of a conventional detecting device.
Figure 3:
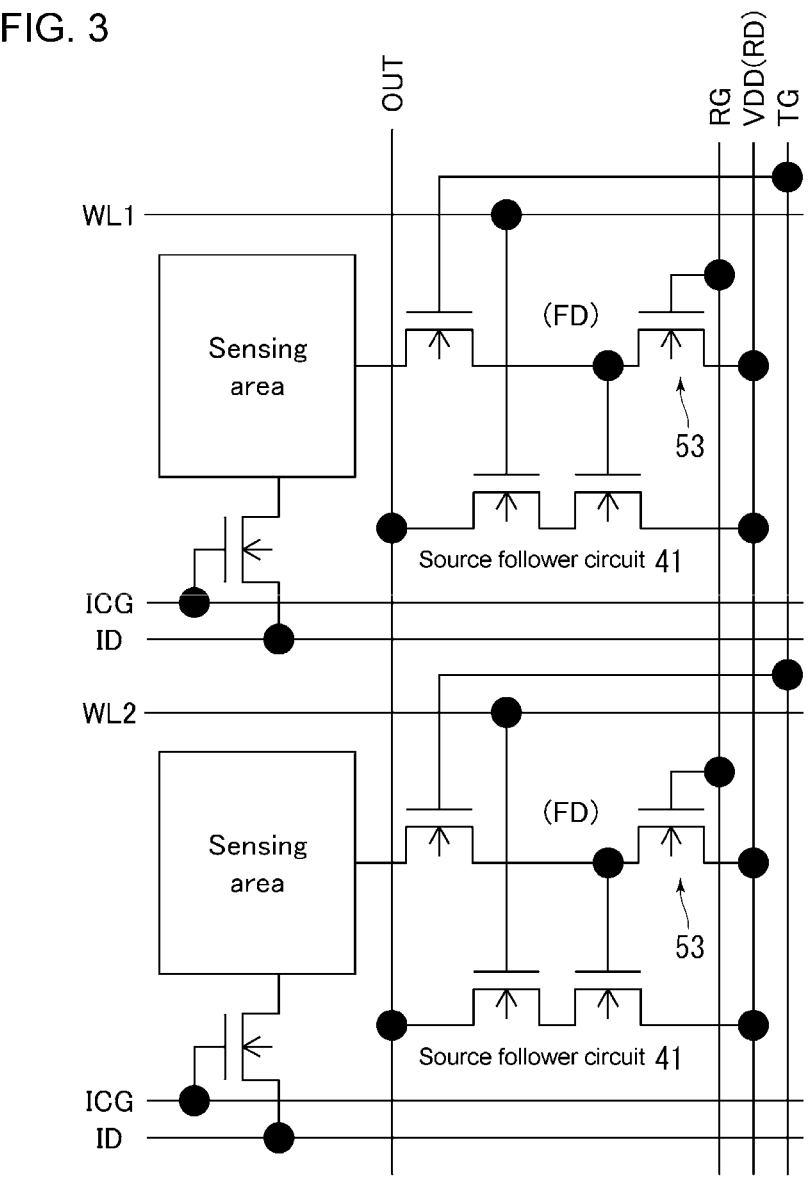
FIG. 3 is a wiring diagram of a conventional detecting device.
Figure 4:
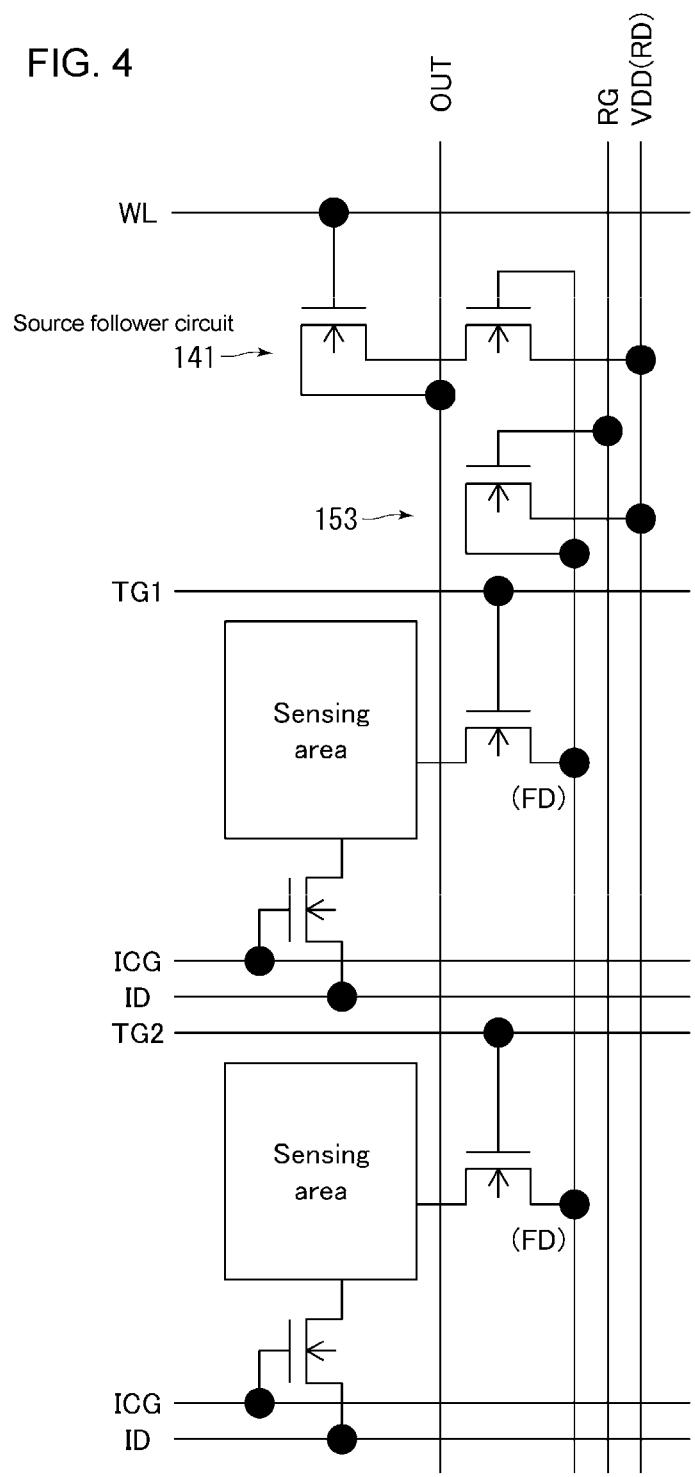
FIG. 4 is a wiring diagram of a detecting device studied in the present specification.
Figure 6:
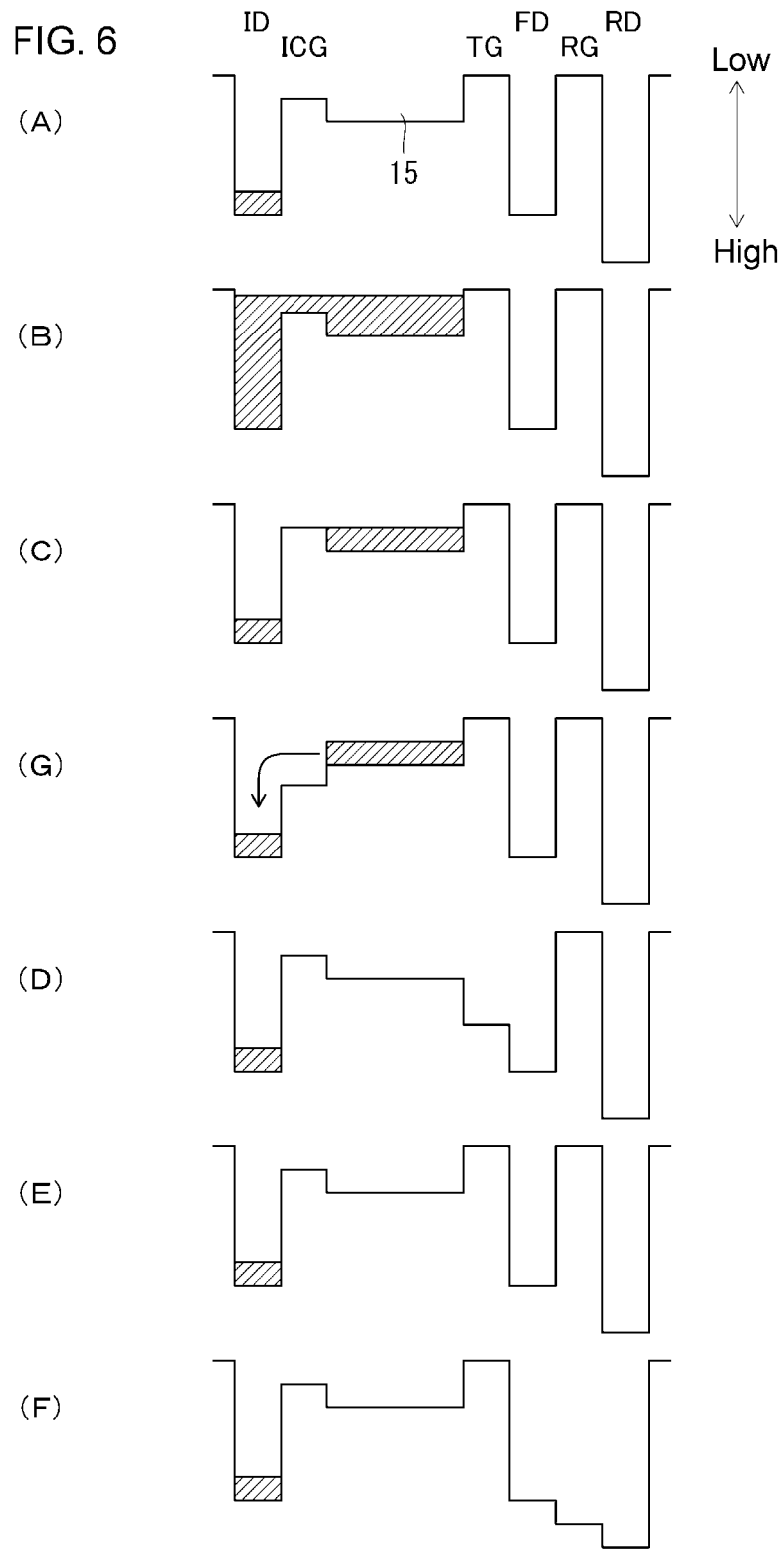
FIG. 6 is an operation flow of the detecting device of FIG. 5.

The charge is supplied from the charge supply section to the first sensing section and the second sensing section as referred to the steps (A)-(C) in FIG. 6 similarly to FIG. 2.

Then, the potential of the ICG section corresponding to the second sensing section is increased to evacuate the charge of the second sensing section to the ID section, as referred to the step (G). Thus, in the second potential well of the second sensing section, the charge is emptied. Next, even if the operations of the steps (D)-(F) are executed similarly to the operations of FIG. 2, a charge is not transferred to the FD section at all.

In the example of FIG. 6, the ICG section is controlled to evacuate the charge of the second sensing section to the ID section. On the other hand, an additional drain may be provided for the second sensing section to evacuate the charge from the second sensing section to the additional drain, for emptying the charge. As such the additional drain used for evacuation, the elimination well with the large capacity and used against the hump of the potential in the disclosure of JP-B-4171820 may be utilized.

In another embodiment of the present invention, the charge is supplied selectively only for the first sensing section and the charge is not supplied for the second sensing section.

In the embodiment, the charge supplying steps as referred to the steps (A)-(C) of FIG. 2 are executed in the operation (i) described below.

Namely, in the operation (i), only in the selected pixel, the steps (A)-(C) of FIG. 2 are executed according to the following operations (i-i) and (i-ii).

According to the operation (i-i), in all of the pixels, the same operation is executed in each of the ICG sections. Then, only in the selected pixel, the ID section may be selectively activated to supply the charge from such the ID section.

According to the operation (i-ii), in all of the pixels, the same operation is executed in each of the ID sections. Then, the potential of the ICG section corresponding to the non-selected pixel having the second sensing section may be controlled and decreased, to prevent the ID section from supplying the charge to the second sensing section in the step (B).

In case that the operations (i-i) and (i-ii) described above are executed, in each pixel, the ICG section control line or the ID section control line can be shared in common.

Figure 7:
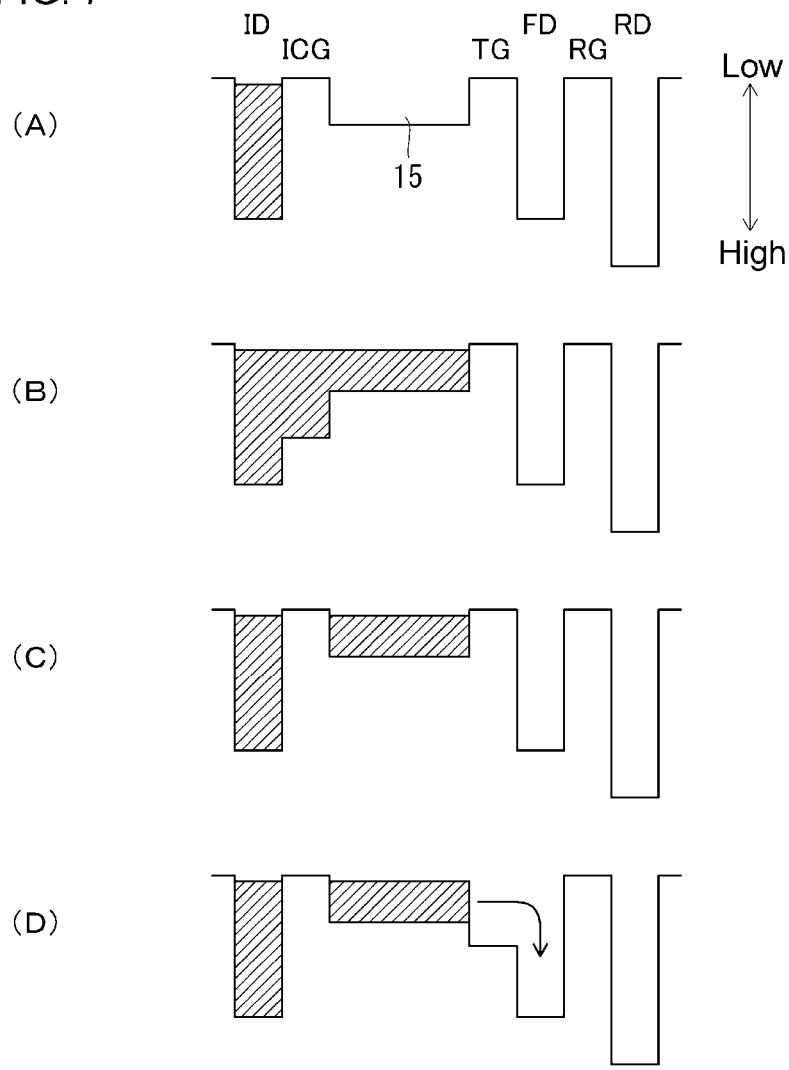
FIG. 7 is another operation flow of the detecting device of FIG. 5.

FIG. 7 shows another method for supplying the charge.

In an example of FIG. 7, the ID section is always charged with the charge. Then, the lowest potential of the charge is lower than the possibly lowest potential of the potential well 15 and is higher than the lowest potential of the TG section, as referred to FIG. 7(A).

Next, the potential of the ICG section is set higher than the bottom potential of the potential well 15 to fill the potential well 15 with the charge, as referred to FIG. 7(B). Incidentally, the ID section is always placed in condition for supplying the charge to keep the lowest potential of the charge.

Next, the potential of the ICG section is set low enough to break up the charge into the charge of the ID section and the charge of potential well 15, as referred to FIG. 7(C). Then, the potential of the TG section is increased to transfer the charge of the potential well 15 to the FD section, as referred to FIG. 7(D).

Incidentally, the charge detection and the charge evacuation are executed in the processes similar to the steps (E) and (F) of FIG. 2.

In the method for supplying the charge shown in FIG. 7, the slash off operation in the steps (B) and (C) of FIG. 2 is not included. So, the method shown in FIG. 7 can eliminates the effect caused by the potential bump.

In addition, the operation for increasing and decreasing the potential of the ICG section can be executed more rapidly than the method of FIG. 2 which necessitates the operations for charging and discharging the ID section. The inventors conceive that the period required for the steps (B) and (C) of FIG. 7 which separate the charge of the ID section and the charge of the potential well 15 can be reduced between ½ and ⅕ of the period required for the steps (B) and (C) of FIG. 2 which slash off the charge.

Incidentally, the electrode of the ICG section is preferred to introduce the potential gradient which is higher in the ID section side and lower in the sensing section side so that the charge faced with the electrode of the ICG section is transferred to the ID section side more rapidly.

The charge supply shown in the steps (A)-(C) of FIG. 7 is executed only for the selected pixel. Namely, the pixels can be divided into the active pixel that the potential well of the sensing region is filled with the charge and the non-active pixel that the potential well is empty of the charge.

In the method shown in FIG. 7, since the potential of the ID section is always made constant, the ID section control line can be shared in common in each pixel.

Incidentally, after the step (C) of FIG. 7, the steps (G) and (D)-(F) of FIG. 6 may be continued.

As described above, the TG section of the pixel provided with the first sensing region holding the charge in the potential well and the TG section of the pixel provided with the second sensing region empty of the charge are opened simultaneously to transfer the charge from each of the sensing sections to the source follower circuit 141 shared in common.

In the integrated body of pixels, the pixels which share the source follower circuit 141 in common can be arbitrary selected. Preferably, groups of pixels which share the source follower circuit 141 in common are distributed evenly.

Each of the pixels which share the source follower circuit 141 in common is preferably located symmetrically around the common element including the source follower circuit and so forth and located further around the wiring region extended from the common element.

Thus, as to the common pixel, the TG section control line is also shared in common, to prevent the increase of the wiring region.

As described above, the present invention is explained on the premise that the source follower circuit is shared in common. Incidentally, regardless of the source follower circuit shared in common, the TG section control line is shared in common, to synchronize the control of the TG section of each pixel, and control the active condition of each pixel on a basis of the existence or the non-existence of the charge in each of the pixels. Thus, the control method suited for the integration is presented.

The embodiment of the present invention is explained in the following.

Figure 5:
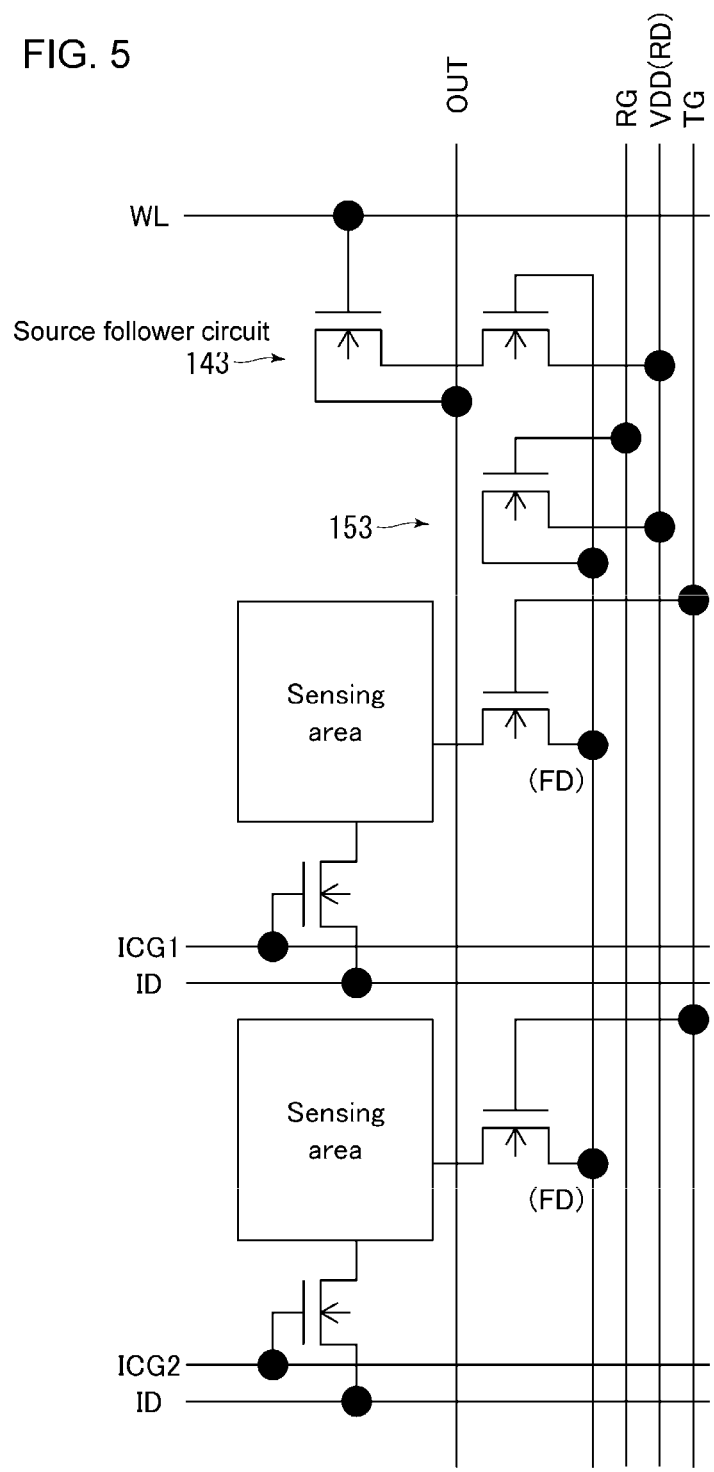
FIG. 5 is a wiring diagram of a detecting device of an embodiment of the present specification.

A detecting device provided with two sensing sections which share a TG control line in common for opening and closing the TG control line at the same timing is explained as one unit in the following. An array circuit provided with four units U11, U12, U21 and U22 is shown in FIG. 9. The circuit configuration of each unit is shown in FIG. 5. When the unit is constituted by the circuit of FIG. 8, the two OUT lines are connected to the charge quantity detecting control section.

In FIG. 9, the numeral 301 indicates the sensing control section. Such the sensing control section 301 is provided with the charge supply control section 303, the TG control section 305, the charge quantity detecting control section 311 and the charge eliminating control section 313. The sensing control section 301 can be constituted by a general-purpose computer.

The charge supply control section 303 controls the potentials applied to ICG1, ICG2, and ID. According such the configuration, in each unit, either of the sensing sections (Pixel) is set active or non-active.

The TG control line 305 is connected to the TG line. The TG line is connected to the gate section provided between the sensing section and the source follower circuit of the FD section in all of the units, to open and close such the elements at the same timing.

The charge quantity control section 311 applies the readout signal to the readout lines WL1 and WL2 of each sensing section, to read out the output of the corresponding output lines OUT1 and OUT2. The output of the source follower circuit is outputted to the output lines OUT1 and OUT2.

The charge eliminating control section 315 controls the potential of the RG line and the VDD line to eliminate the charge stored in the source follower circuit of the FD section.

The operation of the detecting device 300 of the embodiment is explained in the following.

Figure 10:
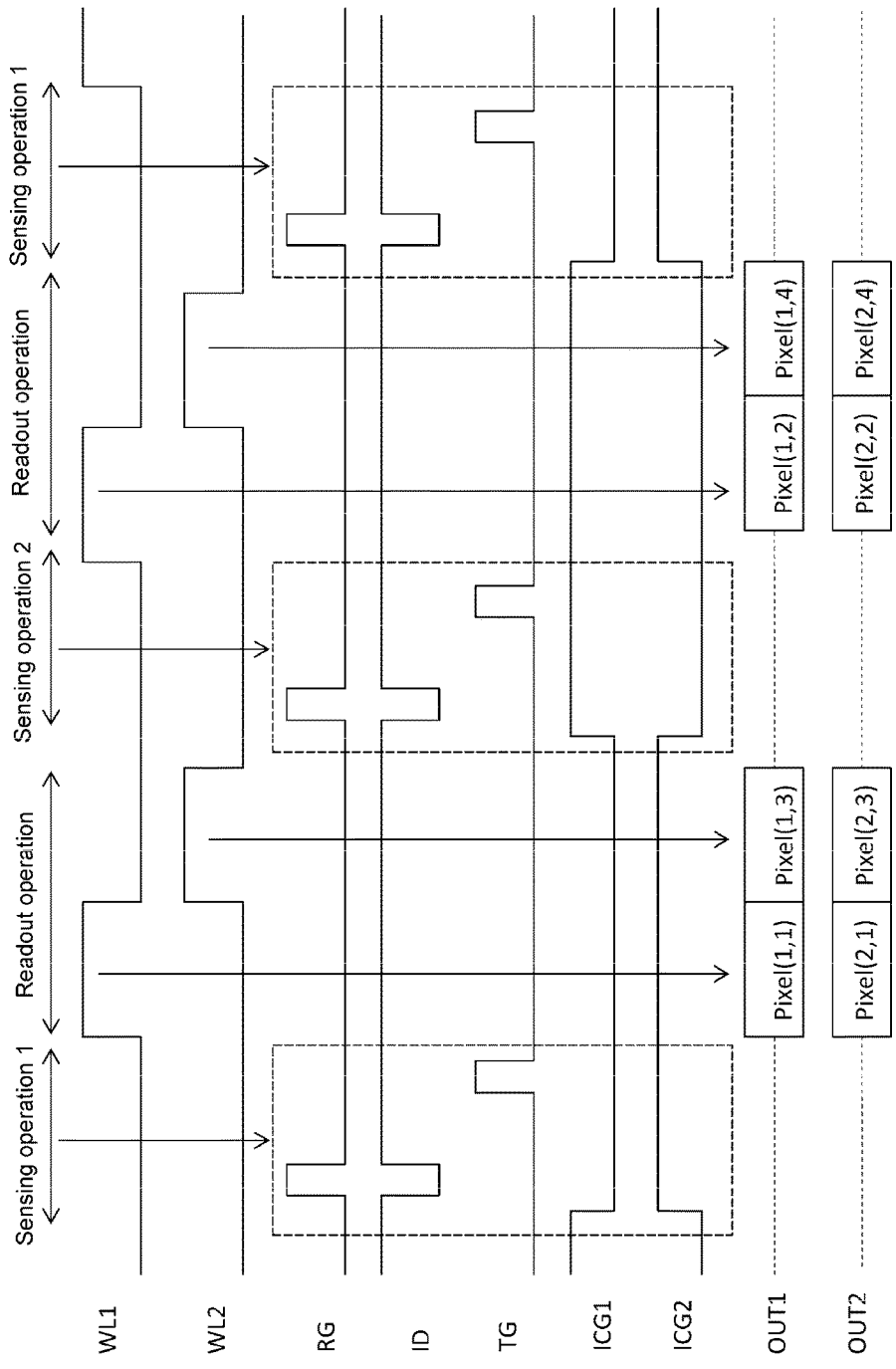
FIG. 10 is a timing chart showing an operation of a detecting device of an embodiment.
Figure 11:
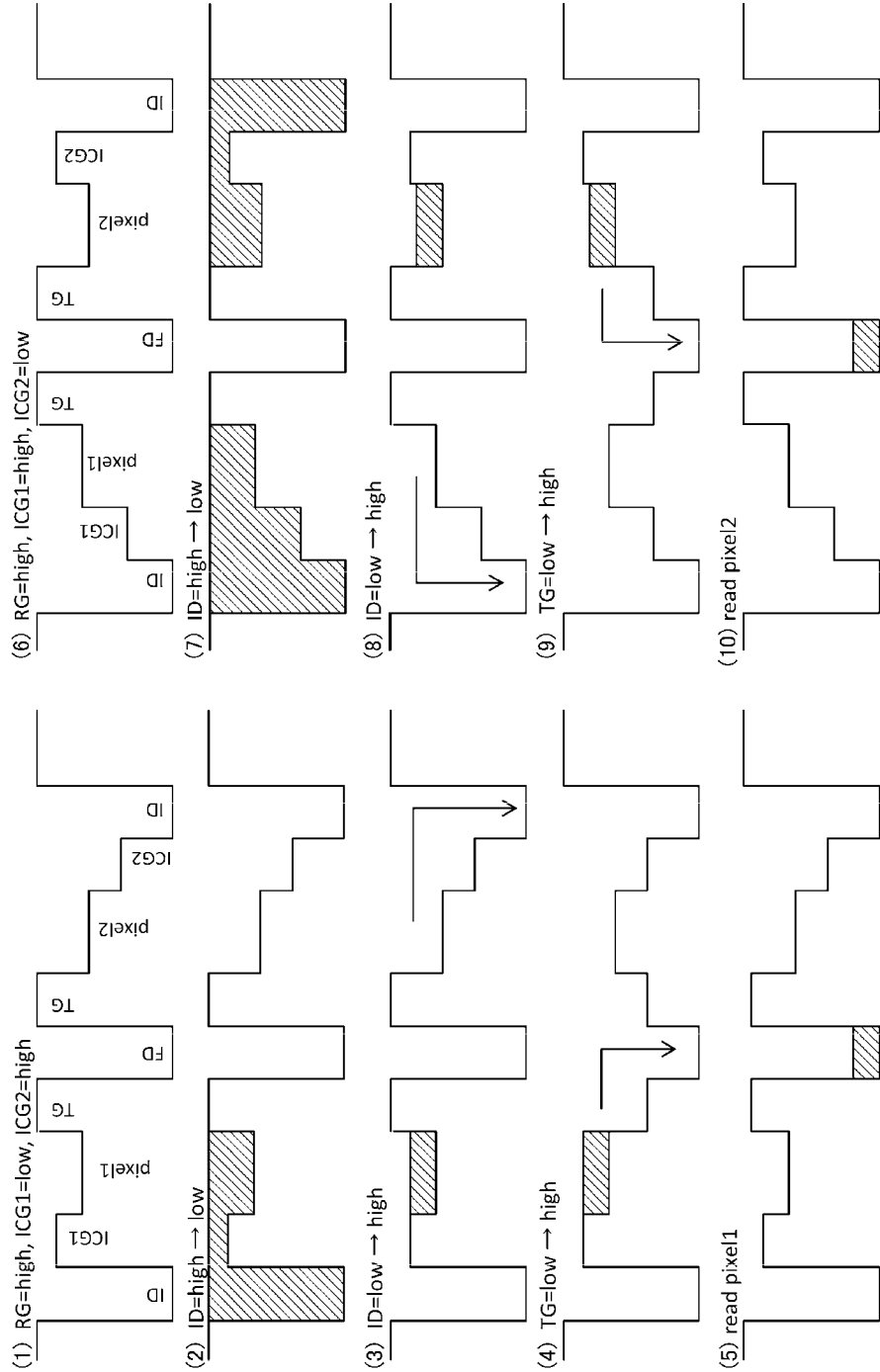
FIG. 11 is an operation flow of a detecting device.
Figure 12:
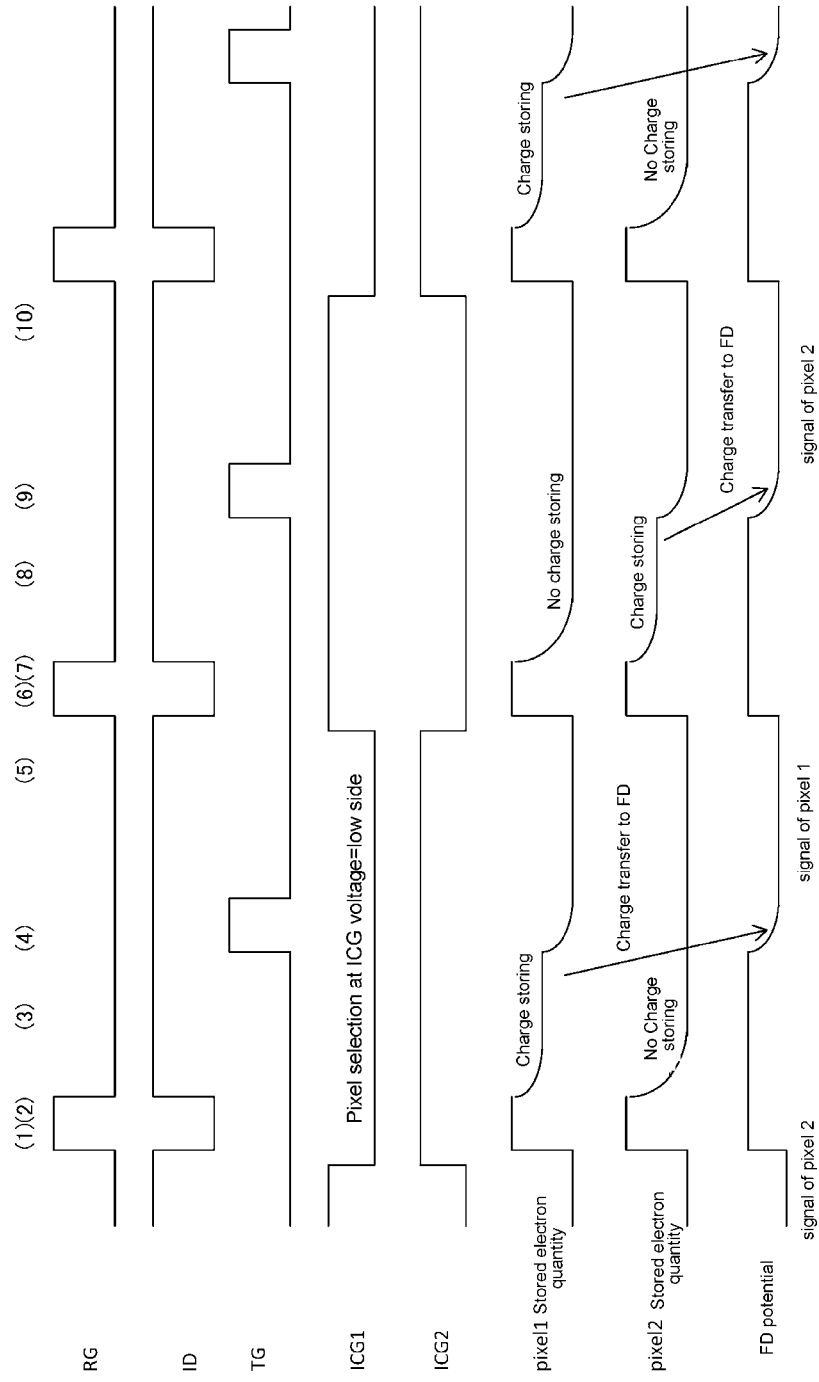
FIG. 12 shows the potential of the respective elements at the respective stages of the operation flow shown in FIG. 11.

FIG. 10 shows the timing chart of the detecting device 300. FIG. 11 shows the operation flow of the detecting device. FIG. 12 shows in detail the potential of the respective elements at the respective stages of the operation shown in FIG. 11.

In the embodiment, the charge is supplied together to the sensing section (Pixel) of each unit, as referred to the steps (2) and (7) of FIG. 11. Then, the charge is eliminated only from the designated sensing section which is not selected, as referred to the steps (3) and (8) of FIG. 11. Namely, the designated sensing section which is not selected is made non-active correspondingly to the second sensing section.

In the steps (4) and (9), each of the TG is opened at the same time to transfer the charge of the sensing section to the readout section, namely the FD section or the source follower circuit.

As to the description above, in the sensing operation 1 shown in FIG. 10, the charge of the pixels (1,1), (1,3), (2,1) and (2,3) is transferred to the FD. In the sensing operation 2, the charge of the pixels (1,2), (1,4), (2,2) and (2,4) is transferred to the FD. During the readout operation after the sensing operation, WLn is sequentially made high, the signal transmitted to the FD is sequentially outputted from OUTn.

In FIG. 11, the charge of the pixel 1(2) is prevented from exceeding the pixel 2 (1), by making the potential of the FD not less than TG=high, to suppress the crosstalk.

Another operation example of the detecting device 300 of the embodiment is explained in the following.

Figure 13:
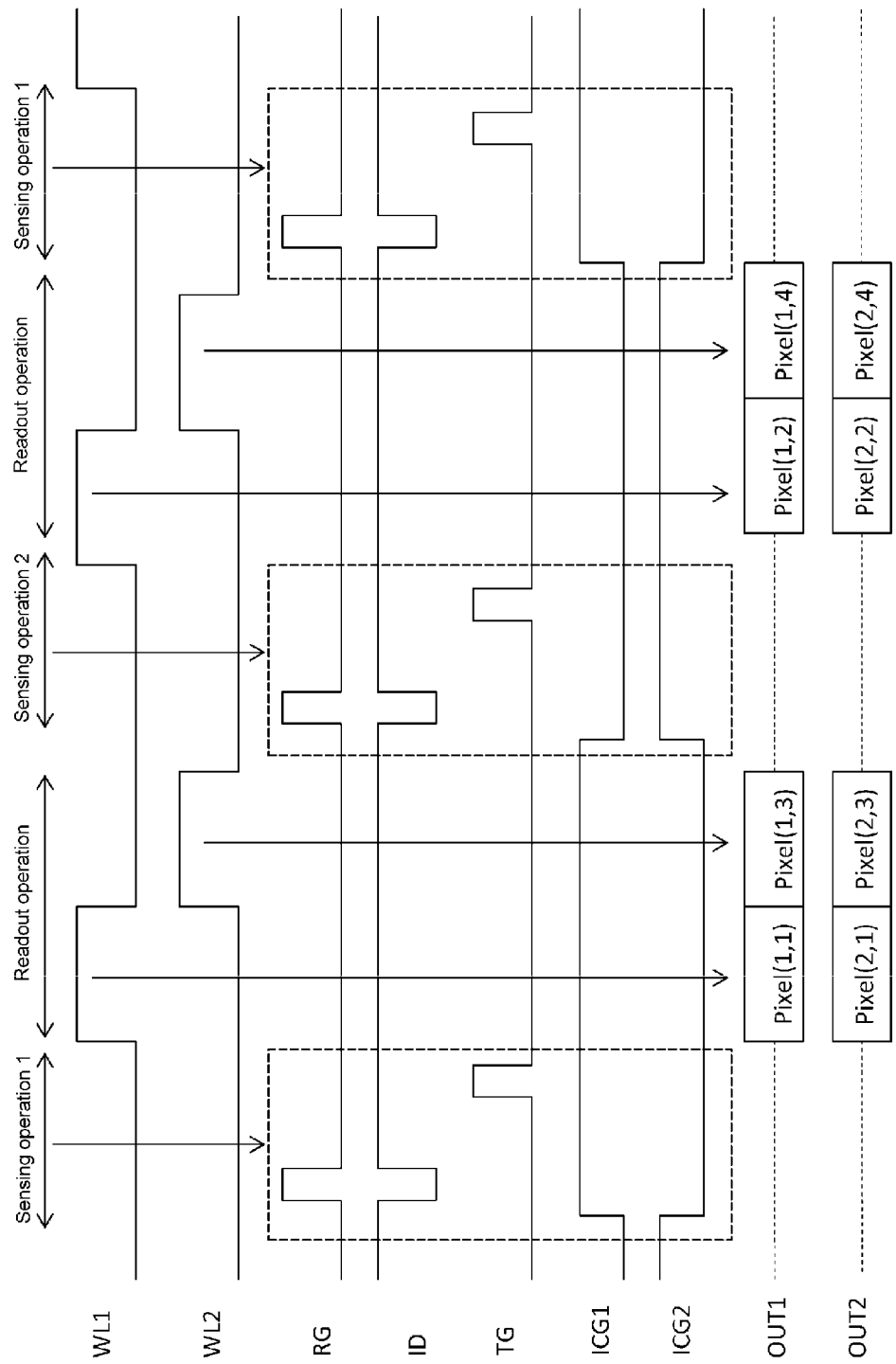
FIG. 13 is a timing chart for showing another operation of a detecting device of an embodiment.
Figure 14:
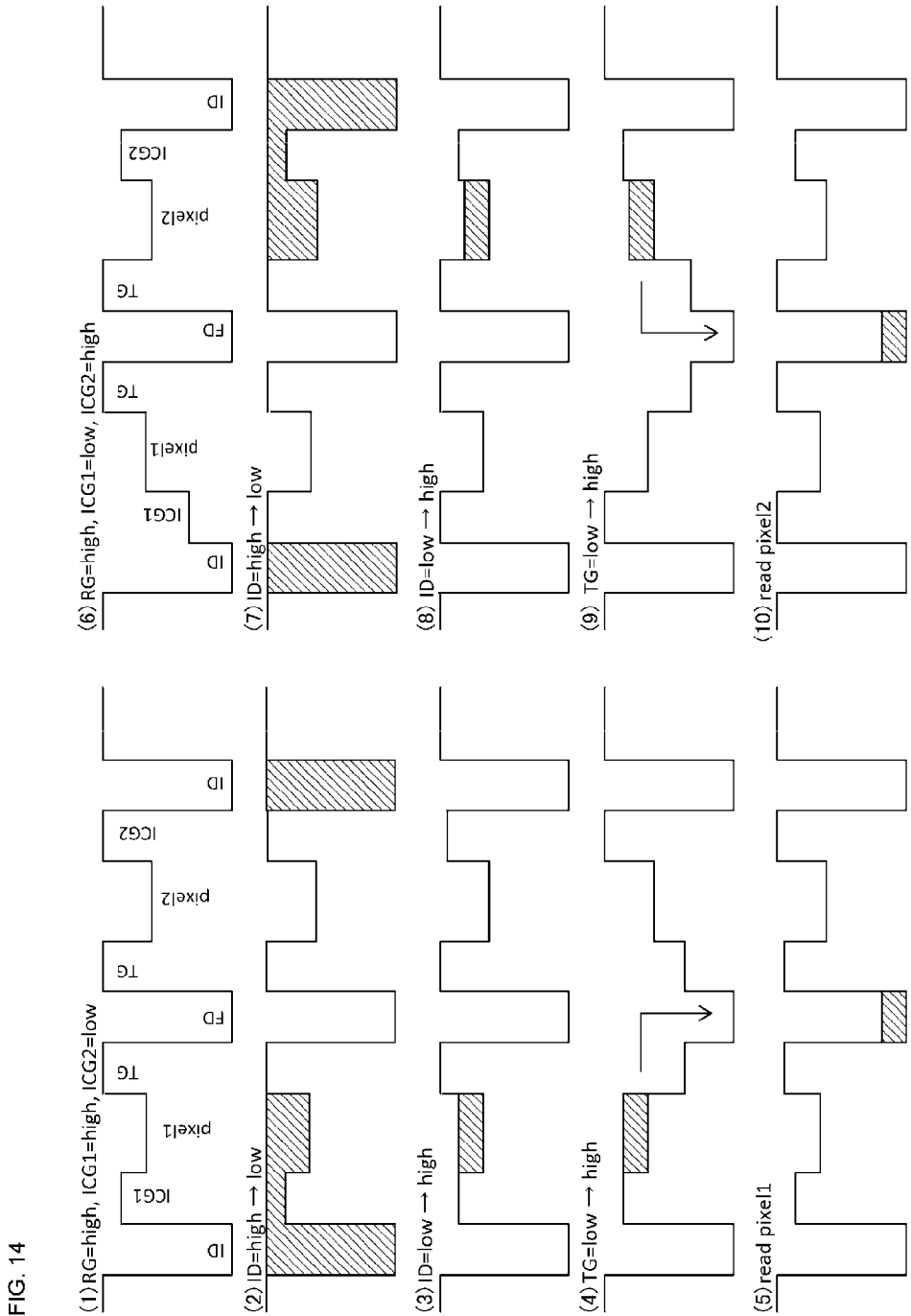
FIG. 14 shows another operation flow of a detecting device.
Figure 15:
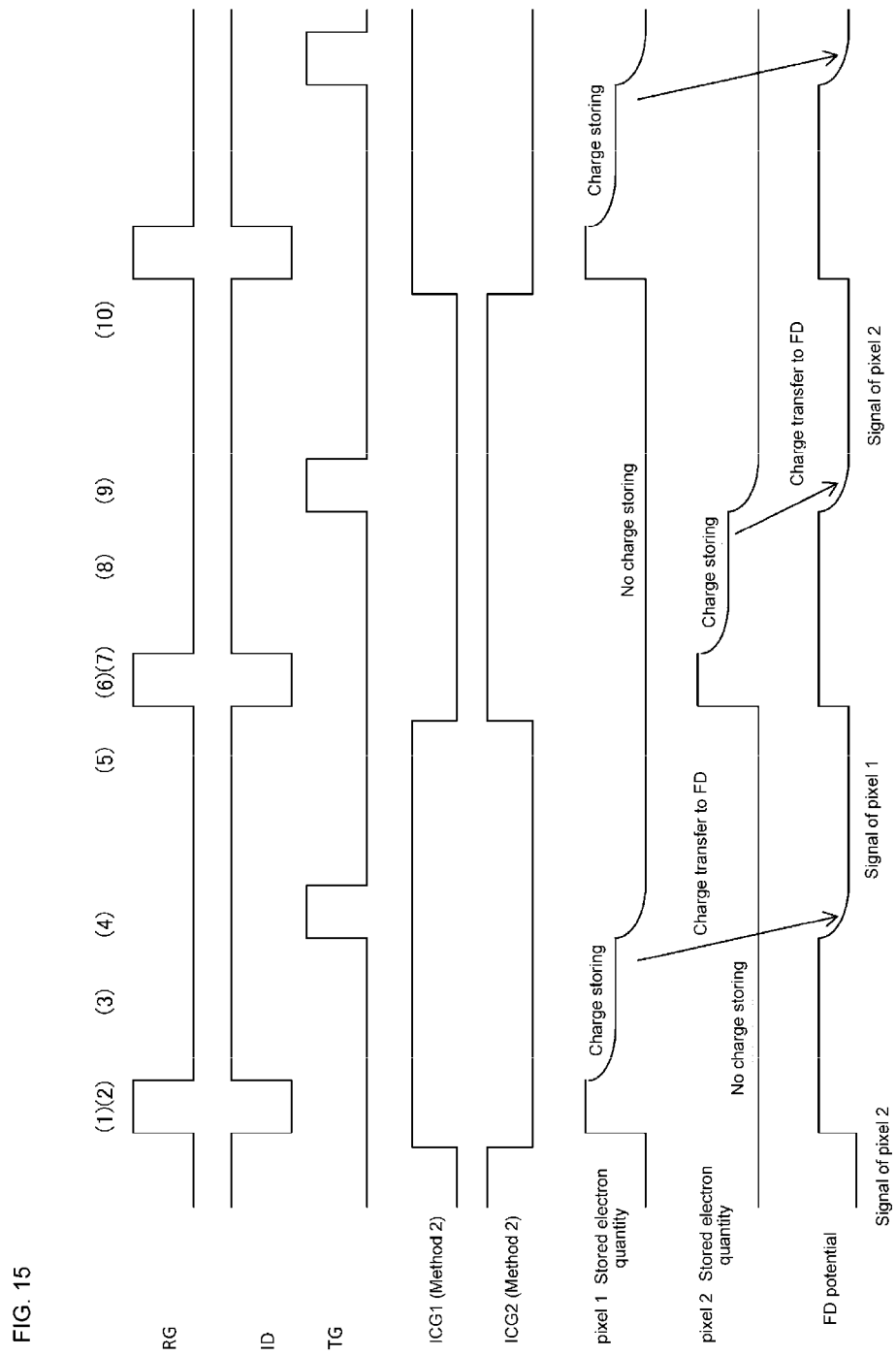
FIG. 15 shows the potential of the respective elements at the respective stages of another operation flow shown in FIG. 14.

FIG. 13 is the timing chart of the detecting device 300. FIG. 14 shows the operation flow of the detecting device. FIG. 15 shows in detail the potential of the respective elements at the respective stages of the operation shown in FIG. 14.

In the example, the charge is supplied only for the sensing section (pixel) in each unit, as referred to the steps (2), (3), (7) and (8) of FIG. 14. The sensing section that the charge supply is rejected is made non-active correspondingly to the second sensing section.

In the steps (4) and (9), the TG is opened at the same time to transfer the charge of the sensing section to the readout section, namely the FD section or the source follower circuit.

As to the description above, in the sensing operation 1 shown in FIG. 13, the charge of the pixels (1,1), (1,3), (2,1) and (2,3) is transferred to the FD. In the sensing operation 2, the charge of the pixels (1,2), (1,4), (2,2) and (2,4) is transferred to the FD. During the readout operation after the sensing operation, WLn is sequentially made high, the signal transmitted to the FD is sequentially outputted from OUTn.

In FIG. 14, when the TG is ON, the charge is not stored in the non-selected pixel to cause no crosstalk.

In case of ID=Low, the ICG potential of the non-selected pixel is set lower than the potential of ID=Low so that the charge is not injected into the non-selected pixel Another operation example of the detecting device 300 of the embodiment is explained in the following.

Figure 16:
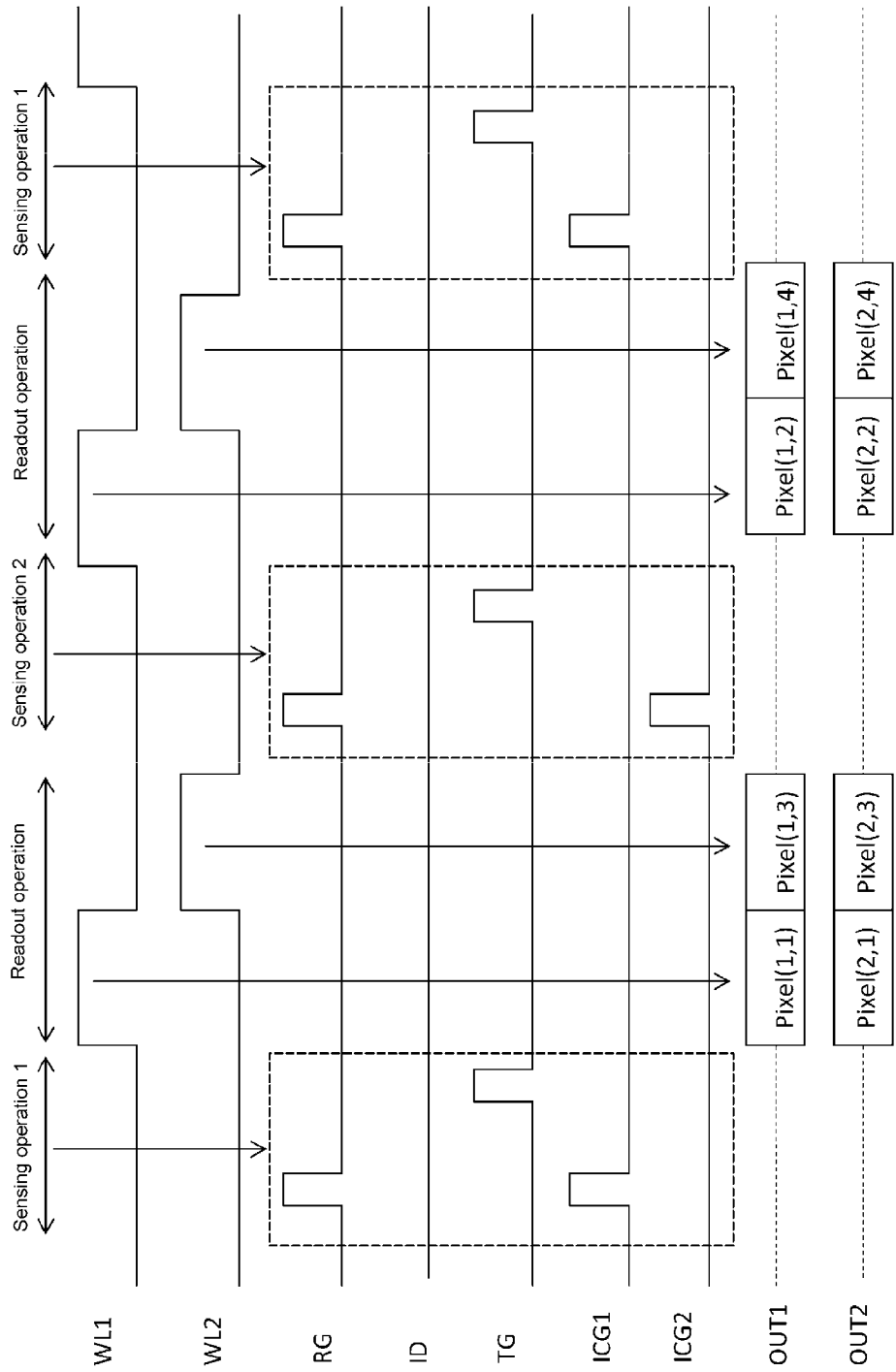
FIG. 16 is a timing chart for showing another operation of a detecting device of an embodiment.
Figure 17:
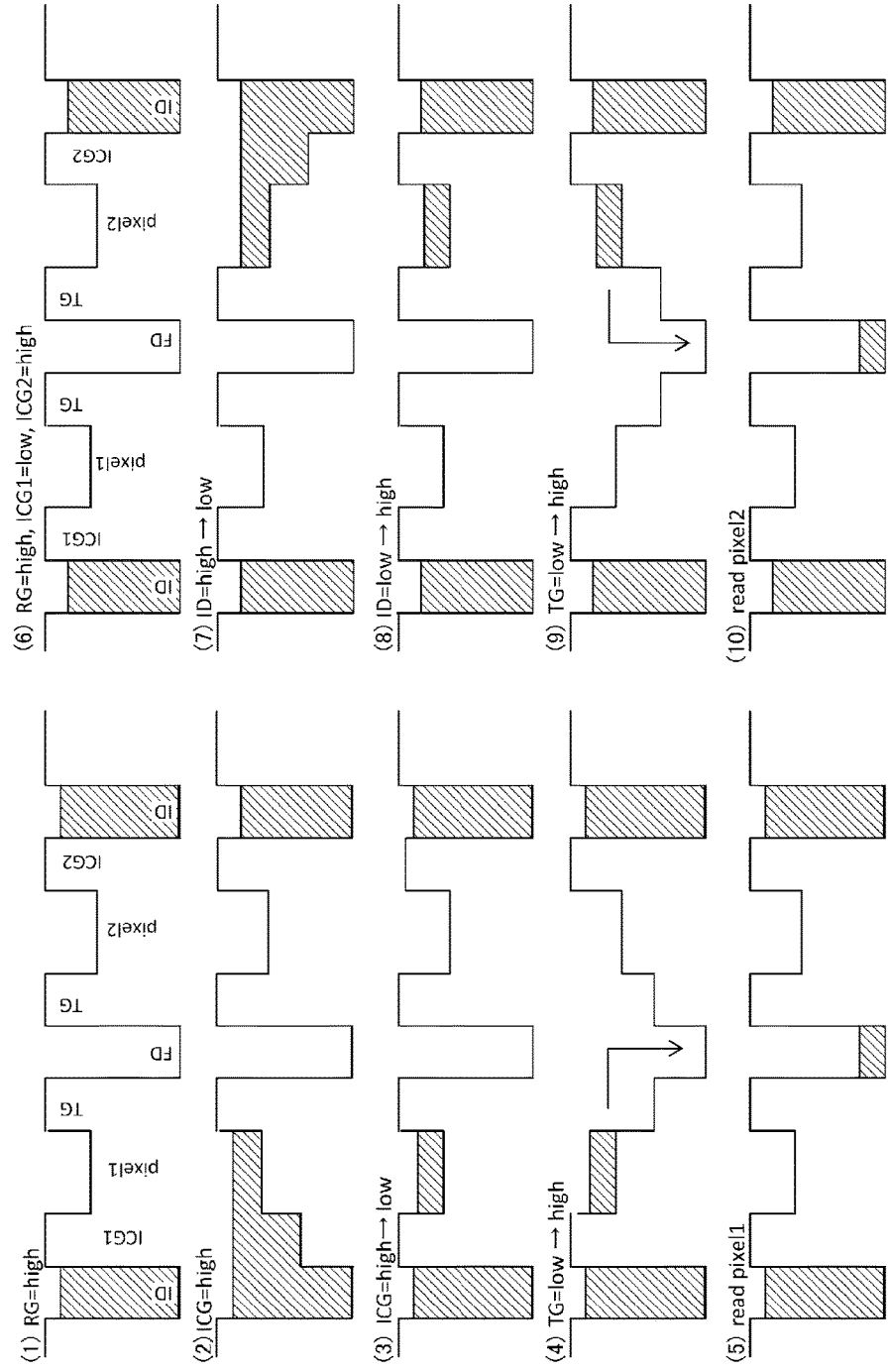
FIG. 17 shows another operation flow of a detecting device.
Figure 18:
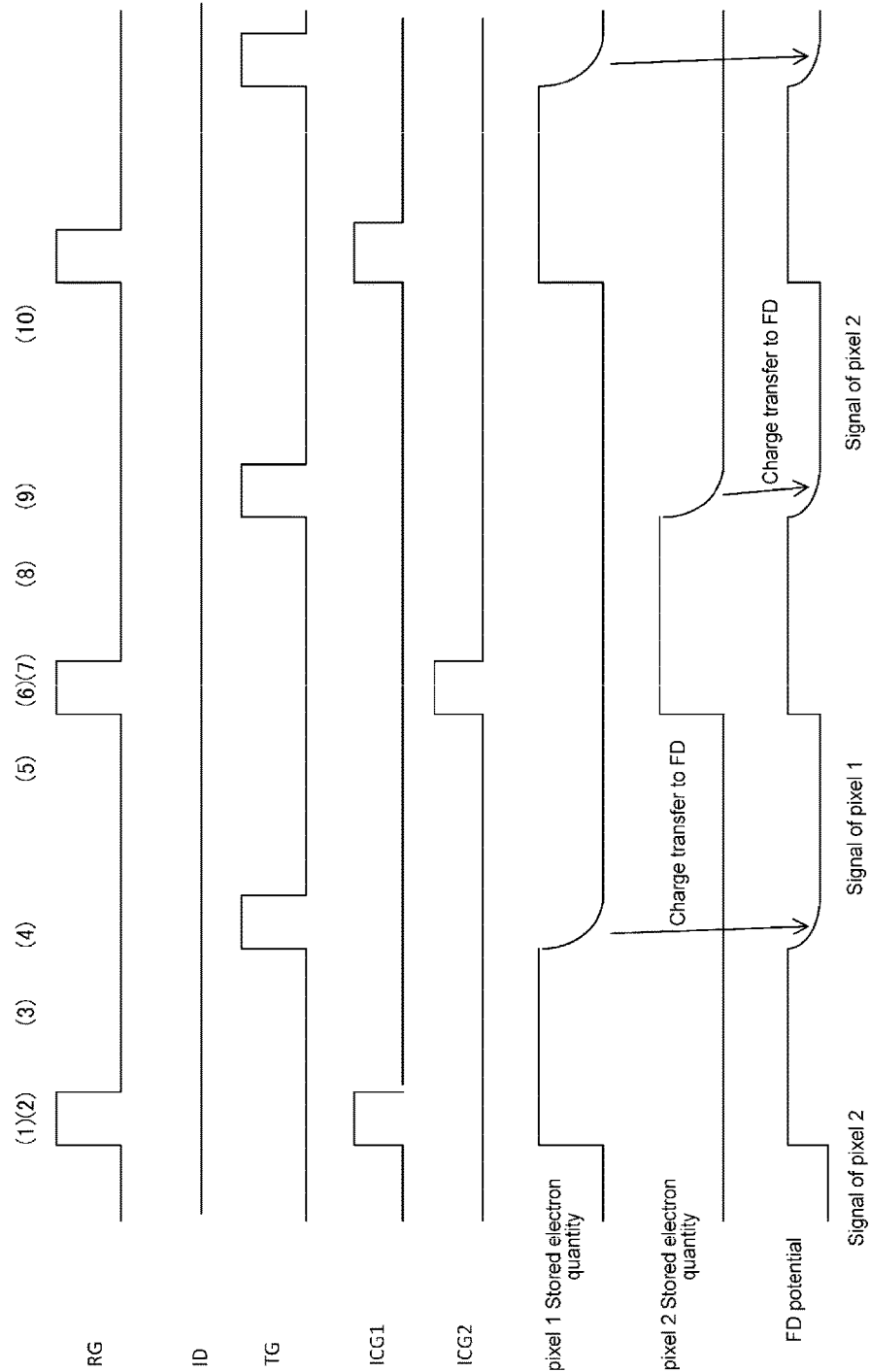
FIG. 18 shows the potential of the respective elements at the respective stages of another operation flow shown in FIG. 17.

FIG. 16 is the timing chart of the detecting device 300. FIG. 17 shows the operation flow of the detecting device. FIG. 18 shows in detail the potential of the respective elements at the respective stages of the operation shown in FIG. 17.

In the example, when the charge is supplied only for the sensing section selected in each unit, the potential of the ICG is made low so that the charge from the ID is not supplied for the non-selected sensing section, as referred to the steps (2) and (7) of FIG. 17. On the other hand, the potential of the ICG is made higher than the potential of the selected sensing section so that the charge is supplied for the selected sensing section, as referred to the steps (3) and (8). Then, the potential of the ICG is made low to divide the charge of the sensing section and the charge of the ID section.

In the steps (4) and (9), the TG is opened at the same time to transfer the charge of the sensing section to the readout section, namely the FD section or the source follower circuit.

As to the description above, in the sensing operation 1 shown in FIG. 16, the charge of the pixels (1,1), (1,3), (2,1) and (2,3) is transferred to the FD. In the sensing operation 2, the charge of the pixels (1,2), (1,4), (2,2) and (2,4) is transferred to the FD. During the readout operation after the sensing operation, WLn is sequentially made high, the signal transmitted to the FD is sequentially outputted from the OUTn.

In FIG. 17, when the TG is ON, the charge is not stored in the non-selected pixel to cause no crosstalk.

The potential of the ID is made constant to control the charge injection by the ON-OFF of the ICG transistor.

The following modified embodiment may be adopted for improving the detecting sensitivity, the detecting rate and the device integration of the chemical and physical phenomenon detecting device.

(The Sensing Section)

For improving the detecting sensitivity, the steps (A)-(D) of FIG. 2 are repeated to detect the charge quantity cumulatively accumulated in the FD section 33, as referred to Japanese Patent JP-B-3623728. The content of JP-B-3623728 is incorporated herein by reference as the content of the present specification.

On the other hand, when the charge is slashed off by the ICG section, as referred to the step (C) of FIG. 2, the small potential bump may be formed in the interface between the ICG section and the potential well correspondingly to the width of the sensing film. If such the potential bump is formed, the redundant charge is left in the sensing section correspondingly to the height of the potential bump. Even if the height of the potential bump is small, in case that the detecting operations are cumulatively repeated, the charge quantity left due to the potential bump cannot be ignored.

So, the eliminating well is formed adjacently to the sensing section or within the sensing section, so that the charge left in the sensing section due to the potential bump is evacuated to the eliminating well. In such a way, the charge quantity transferred from the sensing section to the FD section corresponds exactly to the value of the detected object. Namely, the charge left due to the potential bump is not transferred so that the exact detection can be executed.

Incidentally, the control electrode for controlling the potential of the eliminating electrode is further provided correspondingly to the eliminating well. Such the control electrode is controlled independently of the ICG section and the TG section.

The description above is referred to Japanese patent JP-B-4171820. The content of JP-B-4171820 is incorporated herein by reference as the content of the present specification.

Both of the sensing film formed of silicon nitride and the protective film formed of silicon oxide used for detecting pH as chemical quantity are translucent. So, when the sensing section is used in the open space and so forth, the light which passes through these films produces the charge (electron) in the silicon substrate. If such the charge is stored in the FD section together with the charge supplied from the charge supply section to the sensing section, such the charge could cause the detection error.

So, the detecting device is provided with the means for adjusting the potential of the TG section so as to transfer the charge from the sensing section to the FD section and detecting and storing the first charge quantity in condition that the charge is not supplied from the charge supply section to the sensing section, and the means for adjusting the potential of the TG section so as to transfer the charge of the sensing section 2 to the FD section and detecting and storing the second charge quantity transferred to the FD section in condition that the charge is supplied from the charge supply section to the sensing section. The difference between the second charge quantity and the first charge quantity is calculated to correct the output of the detecting device on a basis of the obtained difference of the charge quantity. Accordingly, the influence of the light can be eliminated from the detected result of the detecting device.

The description above is referred to Japanese patent publication JP-A-2008-79306. The content of JP-A-2008-79306 is incorporated herein by reference as the content of the present specification.

(Light Detection)

The light quantity can be detected by utilizing the fact that the sensing section is activated for the light.

Namely, the light is produced in the sensing section by irradiating the light. Then, by controlling the timing for transferring such the charge to the FD section, the light quantity irradiated in the sensing section can be identified. In this case, the charge supply section is not necessary.

Incidentally, the translucent electrode film is preferably stacked on the sensing section for the spectroscopic detection disclosed in Japanese patent JP-B-4073831. On the other hand, if the translucent electrode film is stacked on the sensing section, the sensing film does not contact the detected object, which makes the pH detection impossible.

(pH and Light Detection)

The light quantity can be detected by utilizing the basic structure of the pH detecting device. By introducing the time difference into the detection, both of pH and the light quantity can be detected by one chip, as referred to Japanese patent JP-B-4183789. The content of JP-B-4183789 is incorporated herein by reference as the content of the present specification.

The charge transfer and storage section may be arranged for pH detection and light detection, as referred to Japanese patent JP-B-4133028. The content of JP-B-4133028 is incorporated herein by reference as the content of the present specification.

The device which can detect pH and the light quantity simultaneously is disclosed in WO/2009/081890A1. The content of WO/2009/081890A1 is incorporated herein by reference as the content of the present specification. In such the device, the charge transfer and storage section for detecting pH by utilizing the electron as the charge and the charge transfer and storage section for detecting the light quantity by utilizing the hole generated by the light irradiation in the sensing section are provided together.

The spectroscopic device and its basic operation are disclosed in Japanese patent JP-B-4073831. In such the spectroscopic device, without the translucent electrode, the control of the potential of the TG section produces the same condition as the potential applied to the sensing section is changed, as referred to WO/2010/106800A1. The content of WO/2010/106800A1 is incorporated herein by reference as the content of the present specification.

Such the spectroscopic device is configured as the following. Namely, the spectroscopic device is provided with the sensing section for generating the charge by the incident light, the charge generation control section for controlling the sensing section between the first state capturing the charge generated from the surface to the first depth of the sensing section and the second state capturing the charge generated from the surface to the second depth of the sensing section, and the FD section for outputting the signal according to the charge quantity captured by the charge generation control section.

The charge generation control section is provided adjacently to the sensing section.

In addition, the spectroscopic device is provided with the TG section for defining the lowest potential of the charge filled in the potential well of the sensing section. With the potential of the TG section controlled, the lowest potential of the charge filled in the potential well is controlled to place the sensing section between the first state and the second state. The charge generated by the incident light overflows the gate section so that the charge is transferred to the FD section. The potential of the TG section is preferred higher than that of the ICG section.

In such the spectroscopic device, for analyzing the exciting light and the light including the fluorescence excited by the exciting light through spectroscopy, the first FD section and the second FD section are provided in order from the side of the sensing section. The capacitance of the first FD is larger than that of the second FD. The first FD is always filled in full with the charge transferred from the sensing section. The charge passing through the first FD is stored in the second FD section. The intensity of each light is identified by the charge quantity stored in the second FD section. Since the capacitance of the second FD section is small, the detection sensitivity can be improved.

The description above is referred to WO/2009/151004. The content of WO/2009/151004 is incorporated herein by reference as the content of the present specification.

Figure 8:
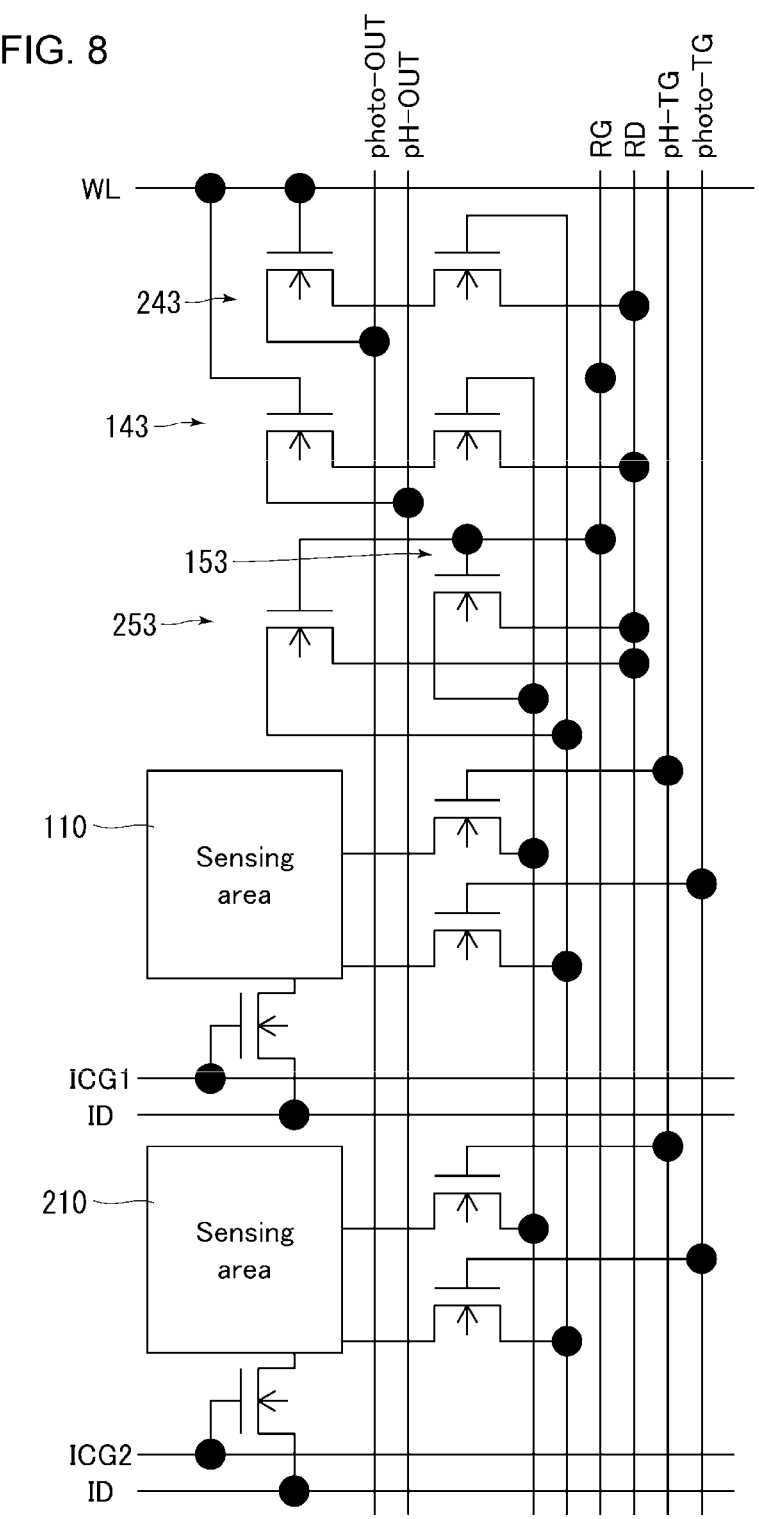
FIG. 8 is a wiring diagram of a detecting device with a function for detecting light quantity.
Figure 9:
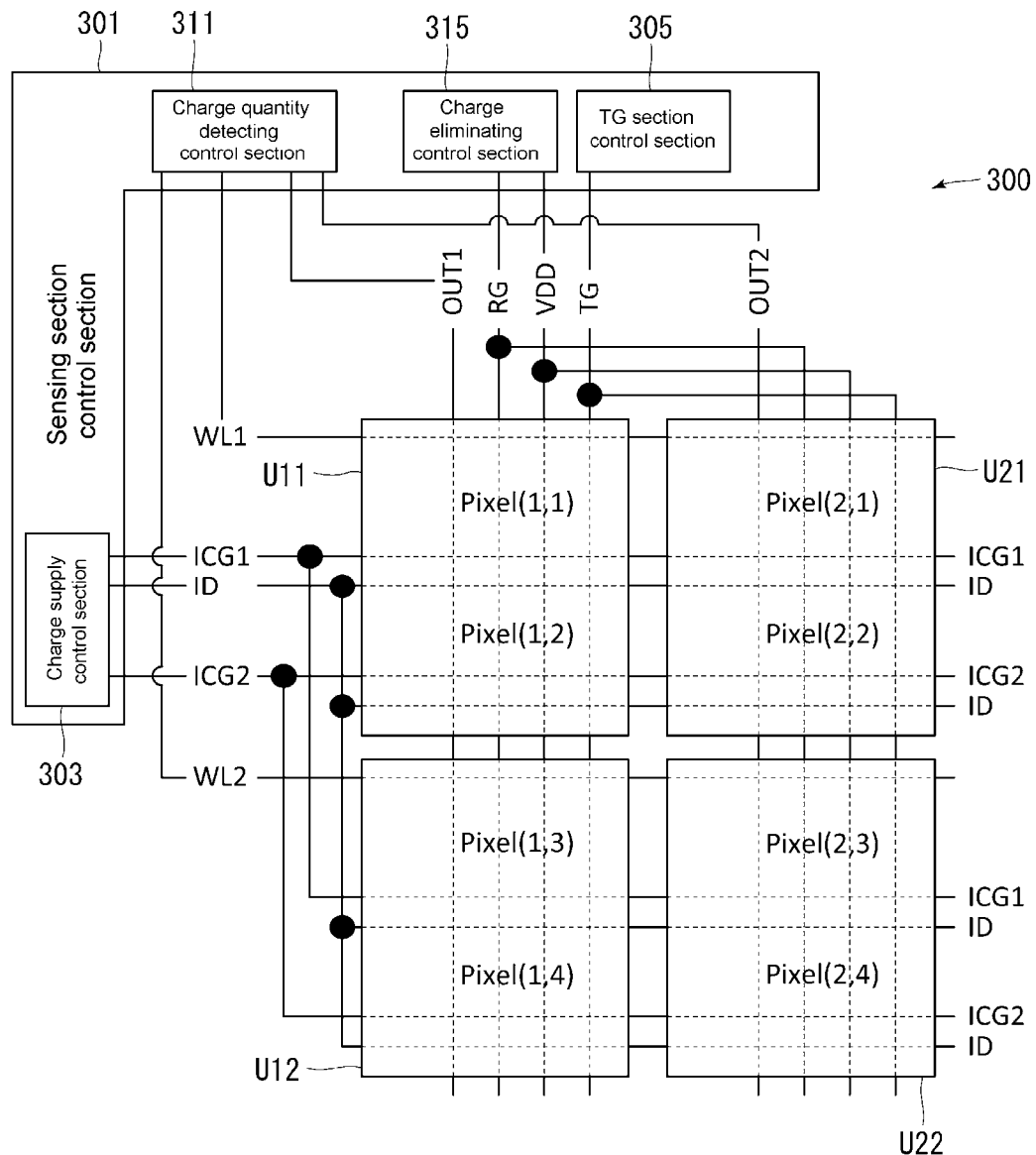
FIG. 9 is a block diagram of an array configuration of a detecting device of an embodiment.

FIG. 8 shows an example of a circuit configuration that a detecting device is provided with a charge transfer and storage section for detecting pH and a charge transfer and storage section for detecting light quantity. Such the example of the circuit configuration is suited for integration.

The same element as that of FIG. 5 is referred to the same reference numeral as that of FIG. 5 and the description thereof is eliminated. In the example, as to the first sensing section 110 and the second sensing section 210, the source follower circuit 143 for detecting pH, the reset circuit 153 for detecting pH, the source follower circuit 243 for detecting the light quantity and the reset circuit 253 for detecting the light quantity are shared in common.

The detecting device for detecting pH executes the same operation as that of FIG. 5.

The detecting device for detecting the light quantity is provided with the charge transfer and storage section with the same structure as that for detecting pH, the charge quantity detecting section and the charge eliminating section. For detecting the light quantity, it is not necessary to supply the charge for the sensing section. The charge generated in the sensing section in response to the light is transferred to the FD, so that the light quantity is identified according to the charge quantity.

When plural detecting devices are used, the variation of the sensitivity is produced in each of the sensing sections. The cause for the variation in sensitivity is attributed to the fact that the sensing film is charged up, for example.

In general, for calibrating the variation in sensitivity, the output signal is obtained as to the standard solution in each of the sensing sections. Such the output signal is calibrated to the exact output signal by the software data processing. However, if the number of the sensing sections increases, the burden imposed on the computer becomes large to prevent the high integration of the device.

So, the inventors of the present invention conceived the idea for calibrating the variation in sensitivity by hardware processing. Namely, the transferred charge quantity as to the standard solution in each of the sensing sections is obtained as the output signal. Next, the difference between such the transferred charge quantity and the standard transferred charge quantity as the standard output signal of the standard sensing section is obtained. Here, the standard sensing section can be selected arbitrarily or theoretically. The charge quantity transferred from the sensing section in contact with the standard solution is uniquely defined as standard transferred charge quantity and used as standard output of all of the sensing sections.

The capacitance of the potential well of the sensing section is changed, or the potential of TG section for transferring the charge is changed, so as to cancel the difference between the standard transferred charge quantity and the transferred charge quantity of each of the sensing sections. Accordingly, the same charge quantity as the charge quantity transferred as to the standard solution from the standard sensing section to the FD section is transferred from the calibrated sensing section to the FD section.

The capacitance of the potential well can be changed by adjusting the potential of the ICG section, the potential of the reference electrode, and/or the bottom potential of the potential well in hardware, for example. The potential of the TG section is adjusted similarly.

Incidentally, depending on the sensitivity required for the detecting device, it is not necessary to calibrate the sensing sections respectively. For example, the difference between the standard transferred charge quantity and the transferred charge quantity from the calibrated sensing section is classified into predetermined value ranges, namely the charge quantity ranges. Next, the value for calibration is predetermined as to each of the predetermined value ranges. Then, the capacitance of the potential well to be calibrated is calibrated by the predetermined value for calibration. Accordingly, the operation for adjusting in hardware is simplified.

The description above is summarized as the following.

A method for controlling a pH detecting device provided with a first sensing section and a second sensing section for changing each bottom potential of each potential well correspondingly to a pH value of a detected object, the pH detecting device transferring a charge of each of the sensing sections to a corresponding FD section through a TG section for identifying pH on a basis of a charge stored in the FD section,
wherein
when the detected object is placed in a first state, for transferring a first quantity of charge from a first potential of the first sensing section and a second potential of the second sensing section to the corresponding FD, a capacitance of one potential of at least one of the sensing section is changed, or a potential of the TG section is changed in transfer of the charge.

In the descriptions above, a pH detecting device is explained as an example of a detecting device. With the selected sensing film, any of chemical and physical phenomena may be applied to the detected object.

The present invention is not limited to the illustrated embodiments or examples alone, but may be changed or modified within the scope of easily devised by those skilled in the art without departing from the spirit of the present invention.

The contents of the related art documents cited in the present specification are incorporated herein by reference as the content of the present specification.

DESCRIPTIONS OF THE REFERENCE NUMERALS 1 pH detecting device
10 Sensing section, 12 Sensing film, 13 Reference electrode, 15 Potential well
20 Charge supply section, 21 ID section, 23 ICG section
30 Charge transfer storage section, 31 TG section, 33 FD section
40 Charge quantity detecting section
50 Charge eliminating section, 51 RG section, 53 RD section
71 Substrate, 72 p diffusion region, 73 n region, 74, 45, 77 n+ region

The invention claimed is:

1. A chemical and physical phenomenon detecting device comprising:
   at least a first sensing section for changing a bottom potential of a potential well and a second sensing section for changing a bottom potential of a potential well, correspondingly to a chemical and physical phenomenon which is a detected object;
   an FD section for storing a charge transferred from each of the sensing sections through a TG section to identify the chemical and physical phenomenon on a basis of the charge stored in the FD section;
   a detecting circuit for detecting a charge stored in one FD section shared in common with the first sensing section and the second sensing section;
   a first TG section directly connected to the first sensing section and the one FD section and a second TG section directly connected to the second sensing section and the one FD section;
   a TG section control section for opening the first TG section and the second TG section at a simultaneous timing; and
   a sensing section control section for holding a charge in the potential well of the first sensing section and emptying a charge out of the potential well of the second sensing section before the first TG section and the second TG section are opened.

2. A chemical and physical phenomenon detecting device according to claim 1,
   wherein
   the sensing section control section comprises a charge supply control section with a charge supplied from an ID section to the first sensing section through a first ICG section and with a charge supplied from the ID section to the second sensing section through a second ICG section, and
   with a potential of the first ICG control section made lower than a potential of the first sensing section by the charge supply control section, the charge supplied from the ID section is held in the first sensing section, and
   with a potential of the second ICG control section made higher than a potential of the second sensing section by the charge supply control section, the charge supplied from the ID section is evacuated from the second sensing section to the ID section.

3. A chemical and physical phenomenon detecting device according to claim 1,
   wherein
   the sensing section control section comprises a charge supply control section with a charge injected from an ID section to the first sensing section through a first ICG section and with a charge injected from the ID section to the second sensing section through a second ICG section, and
   with a control of the first ICG control section by the charge supply control section, the charge is supplied from the ID section to the first sensing section, and
   with a control of the second ICG control section by the charge supply control section, the charge supply from the ID section to the second sensing section is rejected.

4. A chemical and physical phenomenon detecting device according to claim 3,
wherein the charge supply control section being configured so that it making a lowest potential of a charge in the ID section constant,
it making a potential of the first ICG section higher than the lowest potential of the charge in the ID section to supply the charge from the ID section to the first sensing section,
it making the potential of the first ICG section lower than a potential of a first TG section to hold the charge in the first sensing section, and
it making the potential of the second ICG section lower than the lowest potential of the charge in the ID section to reject a charge supply from the ID section to the second sensing section.

5. A chemical and physical phenomenon detecting device according to claim 1,
wherein the sensing section control section provided with a charge evacuation control section, the charge evacuation control section comprising:
a drain section having a potential higher than a bottom potential of each of the sensing sections; and
a second gate section provided between the drain section and each of the sensing section,
wherein
a potential of the second gate section provided continuously to the first sensing section is lower than a potential of the first gate section, and
a potential of the second gate section provided continuously to the second sensing section is higher than a potential of the second sensing section.

6. A chemical and physical phenomenon detecting device according to any one of claims 1-5,
wherein the first TG section and the second TG section are connected to one signal line.

7. A chemical and physical phenomenon detecting device comprising:
at least a first sensing section for changing a bottom potential of a potential well and a second sensing section for changing a bottom potential of a potential well, correspondingly to a chemical and physical phenomenon which is a detected object;
an FD section for storing a charge transferred from each of the sensing sections through a TG section to identify the chemical and physical phenomenon on a basis of the charge stored in the FD section;
a detecting circuit for detecting a charge stored in one FD section shared in common with the first sensing section and the second sensing section;
a first TG section provided between the first sensing section and the one FD section and a second TG section provided between the second sensing section and the one FD section;
a TG section control section for opening the first TG section and the second TG section at a simultaneous timing, the TG section control section having a common control line connecting to both the first TG section and the second TG section; and
a sensing section control section for holding a charge in the potential well of the first sensing section and emptying a charge out of the potential well of the second sensing section before the first TG section and the second TG section are opened.

* * * * *